US008496571B2

(12) United States Patent
Gleim et al.

(10) Patent No.: US 8,496,571 B2
(45) Date of Patent: Jul. 30, 2013

(54) APPARATUS FOR STIMULATING HOMEOSTATIC AUTOREGULATORY MECHANISMS IN THE ORGANISM

(75) Inventors: Peter Gleim, Triesen (LI); Rainer Klopp, Wandlitz (DE)

(73) Assignee: Peter Gleim, Triesen (LI)

( * ) Notice: Subject to any disclaimer, the term of this patent is extended or adjusted under 35 U.S.C. 154(b) by 25 days.

(21) Appl. No.: 13/391,593

(22) PCT Filed: Aug. 20, 2010

(86) PCT No.: PCT/EP2010/062162
§ 371 (c)(1),
(2), (4) Date: Feb. 21, 2012

(87) PCT Pub. No.: WO2011/023634
PCT Pub. Date: Mar. 3, 2011

(65) Prior Publication Data
US 2012/0209055 A1 Aug. 16, 2012

(30) Foreign Application Priority Data
Aug. 25, 2009 (EP) .................................... 09168622

(51) Int. Cl.
*A61N 1/00* (2006.01)
(52) U.S. Cl.
USPC .......................................................... 600/14
(58) Field of Classification Search
USPC ...................................................... 600/9–15
See application file for complete search history.

(56) References Cited

FOREIGN PATENT DOCUMENTS

| DE | 10237519 A1 | 4/2003 |
|---|---|---|
| WO | 0076582 A1 | 12/2000 |
| WO | 2008025731 A1 | 3/2008 |
| WO | 2008127011 A2 | 10/2008 |
| WO | 2009090440 A1 | 7/2009 |

OTHER PUBLICATIONS

Patent Cooperation Treaty, "Notification of Transmittal of Translation of the International Preliminary Report on Patentability—Written Opinion" issued in Parallel International Application No. PCT/EP2010/062162, by Authorized Officer Agnes Wittmann-Regis from The International Bureau of WIPO, mailed Mar. 15, 2012; pp. 1-10.
Patent Cooperation Treaty, "International Search Report" by Authorized Officer Stefan Lohmann; dated Sep. 17, 2010; pp. 1-5.

*Primary Examiner* — John Lacyk
(74) *Attorney, Agent, or Firm* — Duane Morris LLP; J. Rodman Steele, Jr.; Gregory M. Lefkowitz

(57) ABSTRACT

The apparatus consists of a pulse generator, a control device, and a field generating device which jointly generate a pulsed electromagnetic field, wherein series of pulses that have specific intensities and are applied at specific intervals and at different frequencies influence the pulsation of the field, thus making it possible to cause stimulating effects on homeostatic autoregulatory mechanisms in the organism. The pulsed electromagnetic field of the invention achieves greater changes in characteristics and significantly longer decay times than previously known electromagnetic fields. The long-term effectiveness can thereby be prolonged up to ten fold.

10 Claims, 3 Drawing Sheets

APPARATUS FOR STIMULATING HOMEOSTATIC AUTOREGULATORY MECHANISMS IN THE ORGANISM

CROSS REFERENCE TO RELATED APPLICATIONS

This application is a §371 national stage entry of International Application No. PCT/EP2010/062162, filed Aug. 20, 2010, which claims priority to European Patent Application No. EP 09166622.0 filed Aug. 25, 2009, the entire contents of which are incorporated herein by reference.

FIELD OF THE INVENTION

The invention relates to an apparatus for stimulating homeostatic autoregulatory mechanisms in the organism on the basis of a pulsed electromagnetic field.

BACKGROUND OF THE INVENTION

It is already known to influence the microcirculation by means of electromagnetic pulses.

EP 0 995 463 discloses an apparatus which is used to influence biological processes in the human body by means of pulsed electromagnetic fields, in particular in order to increase $O_2$ utilization and to stimulate metabolic processes. The individual pulses can follow a function represented by a formula.

WO 2008/025731 describes an apparatus for generating a pulsed electromagnetic field including periodic pulses with rising and falling envelope curves in accordance with defined measurement data of the microcirculation of the blood.

The object of the invention is to provide an apparatus which serves to achieve stimulatory effects in the microcirculatory system over a prolonged period of time.

Another object of the invention is to provide an apparatus which serves to achieve stimulatory effects in the higher regulation, such as the central nervous system, in particular the vegetative nervous system, preferably also over a prolonged period of time.

According to the invention, the apparatus comprises a pulse generator, a control device and a field generation device which interact to generate a pulsed electromagnetic field, wherein pulse sequences with defined levels, defined intervals and defined frequencies influence the pulsation of the field. In this way, effects stimulating homeostatic autoregulatory mechanisms in the organism can be produced.

When considering which morphological and functional system of the organism allows representative statements about the relevant therapeutic effects of a treatment method to be made, outstanding importance is to be attributed to the blood as a transport organ. The biological function of the blood as an organ consists mainly in its contributions to homeostasis, i.e. to the maintenance of a constant "internal environment" due to the interaction of various control and regulatory processes in order to achieve steady states, and in its contribution to immune responses.

SUMMARY OF THE INVENTION

The most important "constant features" of the organism under physiological conditions are:
water content
composition of the body fluids. Blood constants: e.g. pH=7.3, content of mineral ions (sodium, potassium, magnesium, iron, chloride, phosphate, hydrogencarbonate, protein content), the glucose concentrations are also adjusted to a level with little variation. Maintenance of the blood volume (transcapillary fluid exchange, stop of bleeding, clotting).
body temperature of the (systemic) mean arterial blood pressure.

The living organism is a multistable system in which various morphological units are functionally linked by the blood as an organ in order to ensure homeostasis. These units are the external respiration and metabolism including the cardiopulmonary circulation and the kidney function including blood pressure regulation.

During the complex interaction of control and regulatory processes in the organism in order to maintain homeostasis, all parts of the organism are linked to each other in such a manner that changes in a subsystem (tissue, organ, organ system) have an effect on other subsystems, causing them to achieve a new steady state, wherein the subsystems are coupled to each other by the nerves and by means of the blood circulation, inter alia by the microcirculation.

The functional state of an organ is substantially dependent on the functional state of its microcirculation. It is generally accepted today that most functional disorders or diseases of the organs are at least determined in their development, or even caused, by microcirculatory disorders. Microcirculatory disorders often develop as a consequence of macrocirculatory disorders and can gradually develop their own dynamics which has a major effect on, or even dominates, the development of the disease, regardless of macrocirculatory processes. Without adequate contribution of the microcirculation, i.e. of the transport processes through the microvessels, functional improvements, healing or restitution processes or regeneration processes in the organs are not possible. If the microcirculation is impaired, the symptoms of disorders or diseases can at best be influenced temporarily and to a minor extent, if at all.

The morphological and functional system of the microcirculation is therefore a particularly good indicator of relevant therapeutic and prophylactic effects.

The apparatus according to the invention is intended, above all, to cause defined effects in the microcirculatory system of the blood and to make them visible and verifiable by means of scientifically proven measuring methods and measurement criteria.

The object of the invention is to achieve more significant feature changes for local regulatory mechanisms of the microcirculation of the blood. Another object is to achieve such feature changes over a longer period of time.

Another object of the invention, in addition to feature changes in the microcirculation of the blood, is to positively influence processes of homeostatic regulation of the whole organism and in this manner to improve the physical and mental performance of human beings.

The apparatus according to the invention, which comprises a pulse generator, a control device and a field generation device, is characterized in that the pulse generator is designed to interact with the control device and the field generation device so as to generate a pulsed electromagnetic field by emitting pulse sequences, wherein the pulse sequences on a time axis starting with zero are as follows:
Sequence 1: 0 µT for 2-5 seconds,
Sequence 2: 3-35 µT base signal for 18-22 seconds,
Sequence 3: 30-120 µT additional signal for 100-200 milliseconds,
Sequence 4: sequences 2 and 3 are repeated two to three times, Sequence 5: 0 µT for 2-5 seconds after 60-75 seconds on the time axis, Sequence 6: 3-35 µT base signal for 18-22 seconds, Sequence 7: 30-120 µT additional signal for 100-200 milliseconds, Sequence 8: 3-35 µT base signal for 18-22 seconds, Sequence 9: 30-120 µT additional signal for 100-200 milliseconds, Sequence 10: 0 µT for 2-5 seconds, wherein all sequences are repeated multiple times in the specified order after 100 to 130 seconds on the time axis and wherein the frequency in sequences 2 and 3 ranges from 30-35 Hz and the frequency in sequences 6 to 9 ranges from 8-15 Hz, the additional signal in all frequencies is at least 20 µT above the base signal and the amplitudes of the individual pulses follow an exponential function or rising and falling envelope curves with a harmonic or anharmonic pattern.

The field generation device is a hand-held device including an individual coil and a relatively small pulse emitting surface area of less than 100 cm² (intensive applicator) or a large coil mat for whole-body treatment.

Preferably the field generation device is a coil mat.

In such a coil mat, multiple individual electromagnetic coils can be distributed evenly or unevenly throughout the entire surface area of the mat in order to produce a flat magnetic field. Depending on the size of the mat, said mat can also contain only a single coil.

The individual coils are advantageously designed as conductor loops with an identical surface area or as conductor loops with different surface areas or as a combination of both variants.

In an advantageous embodiment of the invention the pulse generator is designed such that in the pulse sequences the additional signal is at least 35 µT above the base signal, in particular at least 45 µT above the base signal, in all sequences. Particularly preferably the additional signal has an intensity of at least 80 µT.

For the purpose of the invention, the term "base signal" means that the maxima of the individual oscillations within the predefined time unit are essentially the same and do not exceed the predefined intensity value, i.e. for example are not greater than 35 µT.

The base signal consists of a sequence of individual pulses with a pulse width of approx. 33 ms at the aforementioned level of 3-35 µT, for example of 15 µT, for the predefined period of 18-22 s. This is followed by an additional pulse with a pulse width of 100-200 ms with an intensity (intensity=pulse strength=electromagnetic flux density) of 30-120 µT, for example of 70 µT, i.e. 55 µT above the base pulse.

For the purpose of the invention, the term "additional signal" means therefore that, at a defined time and for a very short period of time, here 100-200 ms, a clearly stronger signal with an intensity exceeding the base signal by at least 20 µT is additionally emitted, wherein the additional signal is superimposed on the base signal for said short period of time.

The pulse sequences consist of individual pulses whose amplitudes follow e.g. an exponential function. A preferred exponential function is described in EP 995463 B1 as $y = x^3 \cdot e^{\sin(x^3)}$, wherein the formula indicates the pattern traced by the amplitude y over the time x. The shape of the individual pulses is then approximately the same as shown in FIG. 2 of EP 995463 B1. The individual pulses can also have non-exponential shapes, being rising and falling envelope curves representing harmonic or anharmonic oscillations, as in WO 2008/025731. Alternating pulse groups representing such oscillations are illustrated e.g. in FIGS. 4c to 4f of WO 2008/025731. As a whole, the pulse groups have an arcuate shape.

Pulses or pulse groups with a stepped or square shape are not a subject-matter of the invention.

Pulse groups with individual pulses whose amplitude corresponds to an e function are preferred for the present invention.

The term "multiple repetition" of the pulse sequences means a repetition of 4 to 10 times. When repeated, the duration of the base signal can vary by 1-2 seconds. Advantageously, the repetition of all sequences on the time axis can range from 115-125 seconds.

The electromagnetic field generated influences, advantageously by means of the level of the base signal, the level of the additional signal and the frequency with which the pulse sequences are repeated, functional features of the body's own regulation of the organism—selected from microcirculatory functional features, neurovegetative features (in particular the humoral and nerval regulation of the circulatory system), immunological features and neurological features.

The microcirulatory functional features include
the number of nodal points perfused with blood cells (nNP)
the changes in the venular flow rate ($\Delta Q_{ven}$)
the changes in venular oxygen utilization ($\Delta pO_2$)
the arteriolar or venular vasomotor state ($A_{VM}$)

The neurovegetative features include
intestinal motility (number of segmental contraction movements within the time unit)
changes in the concentration of endogenous opiate analogues (endorphins) in the venous blood.

The immunological features include
changes in the concentration of ICAM-1 (intercellular adhesion molecule)
adhesion of white blood cells to a defined inner venular wall surface (nWBC/A).

The features of the humoral and central nervous regulation of the circulatory system include
changes in the concentration of adrenaline/noradrenaline in the venous blood
changes in the diameters of the arterioles in the subcutis and in the mucosa of the rectum (arterioles close to the capillaries and arterioles close to the arteries).

The neurological features include
standard EEG
provocative EEG.

With regard to the microcirculatory functional features, the number of nodal points that are currently perfused with blood cells in a defined microvascular network, nNP, is determined taking into account the number of blood-cell perfused branching points in said network as an indicator of the distribution of the blood. The flow velocity limit of the red blood cells is defined to be $v_{RBC} = 80$ µm/s. The evaluation is done in + or − (compared to the defined initial value n=60).

By means of the present invention, using the pulse sequence 1-10 and repeating said pulse sequence four times, the nNP value is, for example, increased by 15-20%, compared to the initial value, and even after 8 hours it is still higher than the initial value. This clearly shows both the immediate effect and the long-term effect of the stimulatory apparatus according to the invention.

The venular flow rate, $Q_{ven}$, and the arteriolar flow rate, $Q_{art}$, define the particle flow (blood cell flow) in defined venules or arterioles. It is given in µm³/s. $\Delta Q_{ven}$ is the change in the venular flow rate and can also be given as a percent change relative to the initial value. By means of the invention, the values $Q_{ven}$ and $Q_{art}$ are significantly increased, this effect lasting for a prolonged period of several hours.

The venular oxygen utilization, $\Delta pO_2$, is given as a percent change relative to the initial value at the time t=0. The absolute difference of the oxygen saturation of the haemoglobin in the arterioles supplying blood and the venules carrying blood away in a network of a selected tissue target is determined. The targets selected are tissue portions of the skin or intestine which comprise large, much branched blood vessel networks representing the circulatory system of the organism and which also belong to the immunologically active organs and are furthermore easy to access for non-invasive measurements. This value is also increased over a prolonged period of time by means of the invention.

The spontaneous arteriolar (or venular) vasomotor state, $A_{VM}$, is determined by determining the distance-time chart of the autorhythmic contraction movements of smooth muscle cells of the arteriolar vessel wall (measurement of the distance made perpendicular to the longitudinal axis of the microvessel from the endothelium surface to the opposite endothelium surface at equidistant measuring times; 60 measured values per second; determination of the combined oscillation; FOURIER analysis; determination of the amplitude-frequency spectrum). The criterion is the surface area, A, below the envelope of the amplitude-frequency spectrum of the arteriolar vasomotion (a combined oscillation). The value is given as a percent change relative to the initial values.

Similar to the nNP value the microcirculatory value $A_{VM}$ for example is increased by 15-25% relative to the base value, and after 8 hours it is still 8 to 10% above said base value.

The stimulatory effects caused by the apparatus according to the invention and the amplitude-modulated and frequency-modulated pulsed electromagnetic field produced by means of said apparatus concern 1. local regulatory mechanisms
of the microcirculation of the blood, such as the spontaneous arteriolar vasomotion, the tonus regulation initiated by the endothelium, the formation and release of NO in the endothelium 2. the vegetative nervous system
e.g. circulatory effects such as nerval control of the regulation of the vessel lumina of large-calibre arterioles, the activities of the glands producing internal secretions as well as hormonal balances, e.g. by changes in the concentration of endogenous opiate analogues (e.g. endorphins) in the venous blood; intestinal motility (number of segmental contraction movements within the time unit)

3. the central nervous system and humoral regulation
such as being awake, being alert, being able to concentrate; changes in the concentration of adrenaline/noradrenaline in the venous blood.

By means of the invention the concentration of adrenaline/noradrenaline is significantly increased, for example.

Furthermore the concentration of, for example, the endorphins in the venous blood is increased by 5-7% relative to the initial value, and after 8 hours the increased value is still 2-3% above the initial value. These are significant increases which are not achieved with other pulse sequences than the pulse sequences of the invention.

With regard to the effect on local regulatory mechanisms, it has been found that the apparatus according to the invention with the pulsed electromagnetic field generated, including the very special pulse sequence, pulse level and pulse duration, serves to achieve both more significant feature changes and, in particular, significantly longer decay times compared to known electromagnetic fields. The long-term effectiveness can thereby be prolonged up to 10-fold. This is particularly surprising in light of the fact that pulses including a base signal and an additional signal in the same frequency range do not show these results.

Moreover, the invention provides prophylactic and complementary therapeutic effects concerning many processes of homeostatic regulation of the whole organism. These include, for example, impaired wound healing/chronic wounds, various therapy-resistant chronic diseases involving macrocirculation and microcirculation, rehabilitation measures, increase in the physical and mental performance of older people, alleviation of age-related ailments, stress-related disorders of blood perfusion and many more, which are improved by means of the invention.

The effects on the vegetative and central nervous system are also very surprising, since previous magnetic field treatments with different pulse sequences did not show any significant results here.

The invention also relates to the provision of a prophylactic or therapeutic method for stimulating local and higher homeostatic autoregulatory mechanisms in the organism, characterized in that the body or a part of the body of a patient is exposed to a pulsed electromagnetic field, wherein the pulse sequences on a time axis starting with zero are as follows:

Sequence 1: 0 µT for 2-5 seconds,
Sequence 2: 3-35 µT base signal for 18-22 seconds,
Sequence 3: 30-120 µT additional signal for 100-200 milliseconds,
Sequence 4: sequences 2 and 3 are repeated two to three times,
Sequence 5: 0 µT for 2-5 seconds after 60-75 seconds on the time axis,
Sequence 6: 3-35 µT base signal for 18-22 seconds,
Sequence 7: 30-120 µT additional signal for 100-200 milliseconds,
Sequence 8: 3-35 µT base signal for 18-22 seconds,
Sequence 9: 30-120 µT additional signal for 100-200 milliseconds,
Sequence 10: 0 µT for 2-5 seconds,
repeating all sequences multiple times in the specified order after 100 to 130 seconds on the time axis over a period of 5-20 minutes, wherein the frequency in sequences 2 and 3 ranges from 30-35 Hz and the frequency in sequences 6 to 9 ranges from 8-15 Hz, the additional signal in all frequencies is at least 20 µT above the base signal and the amplitudes of the individual pulses follow an exponential function or rising and falling envelope curves with a harmonic or anharmonic pattern.

An advantageous period is 8-15 minutes.

The duration of treatment ranges from a one-off treatment to a twice-daily treatment for 5-20 minutes and 1 to 90 days, wherein interruptions of 2-5 days can be planned.

With the coil mat, for example, 2 treatments with a duration of approx. 8 minutes can be made at an interval of 2 hours. These two treatments can be repeated every other day. The treatment intervals can also be longer or shorter, depending on the age, physique, fitness and condition of the person to be treated. Examples include 1 10-minute treatment per day on 5 consecutive days, then a one-week break and then repeating the same treatment once again. The treatment can be continued in this manner for 2-3 months. Treatments which last several months are also possible with 2 or 3 treatments per day, then a break of 2 or 3 days and then another 2 or 3 treatments, etc.

When using a small intensive applicator the duration of treatment can be the same or the intervals can be shorter, in particular with a higher magnetic flux density of the base and the additional signal, e.g. 30-35 µT for the base signal and 100-120 µT for the additional signal.

BRIEF DESCRIPTION OF THE DRAWINGS

The invention will now be explained by means of examples. In the appended drawing.

DETAILED DESCRIPTION

Example 1

The apparatus consists of a pulse generator which is supplied with a mains voltage of 230 V/50 Hz (alternating current), a control device for different field strengths on the applicators and a coil mat as an applicator. The operating voltage of the control device, and hence the nominal power on the coil mat, is max. 12 V (direct current). A preferred apparatus is the BEMER apparatus of Innomed International AG, Liechtenstein. The coil mat has a surface area of 70×170 cm, so as to accommodate the whole or almost the whole body of a patient who is lying down. Three coil pairs are distributed in the coil mat. The electromagnetic flux density of the electromagnetic field and the time intervals are controlled in a series of stages, e.g. 10 stages, by means of the control device.

The apparatus including the pulse generator designed according to the invention is tested in a group of test persons. Number of test persons: 32, divided into a verum group of 16 test persons and a control group of 16 test persons. The test persons were male, aged 56-67 years, exposed to stress.

The verum group was treated as follows:
lying down on the coil mat
pulse sequence (combined oscillations with an arcuate shape)

| Sequence 1: | 0 µT | 3 s | |
| Sequence 2: | 35 µT | 18 s; | 33 Hz |
| Sequence 3: | 80 µT | 120 ms | |
| Sequence 4: | sequences 2 and 3 are repeated three times, | | 33 Hz |
| Sequence 5: | 0 µT | 3 s | |
| Sequence 6: | 35 µT | 20 s; | 12 Hz |
| Sequence 7: | 80 µT | 120 ms | |
| Sequence 8: | 35 µT | 20 s; | 12 Hz |
| Sequence 9: | 80 µT | 120 ms | |
| Sequence 10: | 0 µT | 2 s | | repetition of the pulse sequence for a total of 10 minutes of treatment measurement of the features from time 0 to 480 minutes every 30 minutes (equidistant)

test persons are allowed to get up and walk up and down a few steps after the treatment time.

The control group was treated as follows:
lying down on the coil mat
pulse sequence: none (placebo) for 10 minutes
measurement as in verum group.

The measuring methods used were intravital microscopy, Laser DOPPLER microflow measurement, white-light spectroscopy, intravital microscopic reflection spectroscopy and clinical laboratory diagnostics.

The features selected from the features examined were:
1. Number of nodal points perfused with blood cells, nNP, in a defined tissue unit (V=2000 µm³) in the target tissues, i.e. muscle layer of the rectum and subcutaneous tissue.

Figure 1:
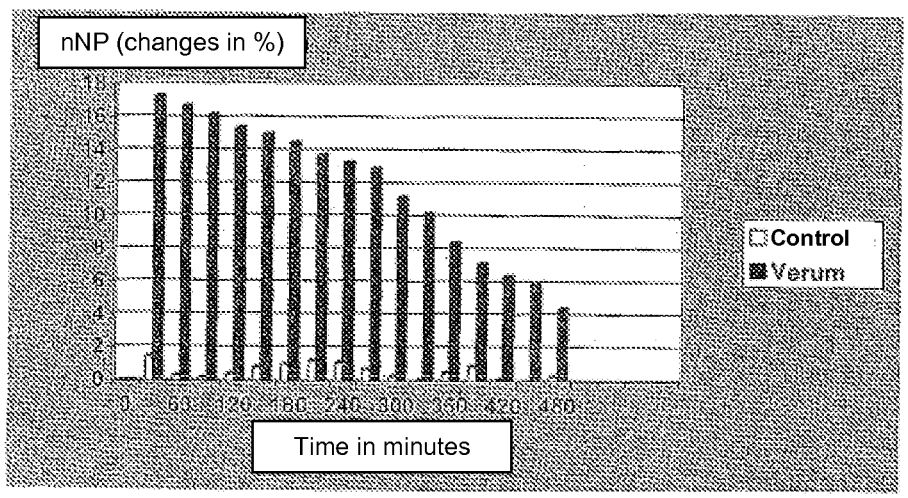
FIG. 1 shows a diagram relating to the nNP feature in the target tissue, i.e. muscle layer of the rectum, following the use of the apparatus according to the invention
Figure 2:
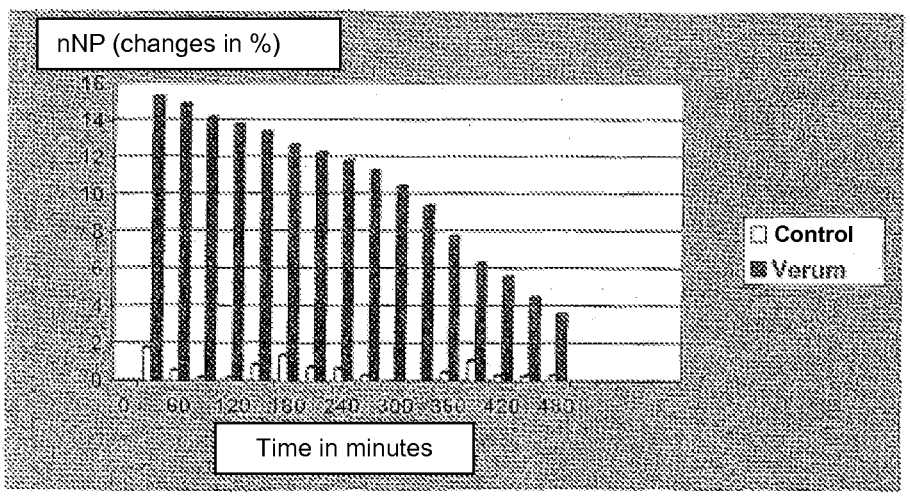
FIG. 2 shows a diagram relating to the nNP feature in the target tissue, i.e. subcutaneous tissue, following the use of the apparatus according to the invention

As can be seen in the illustration in FIG. 1 and FIG. 2, the verum group, unlike the control group, showed a significantly increased change of 17% and 15%, respectively, 30 minutes after treatment and the value of the control group had not been reached even after 8 hours. The decay rate, hence, is surprisingly long and follows a nearly identical pattern in both tissue types.

2. Endorphin concentration, $c_E$, in the microcirculation of a defined tissue volume unit (V=2000 µm³) in the target tissues, i.e. muscle layer of the rectum and subcutaneous tissue.

Figure 3:
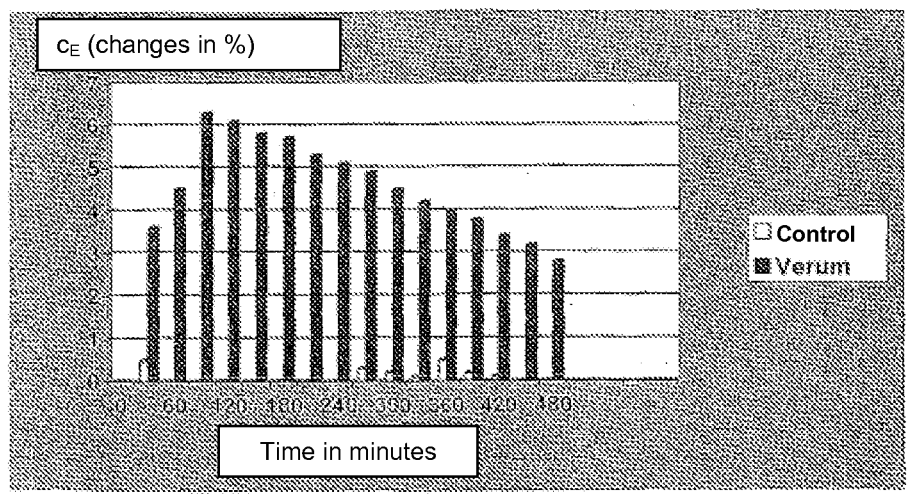
FIG. 3 shows a diagram relating to the feature change in endorphin concentration $c_E$ in the target tissue, i.e. muscle layer of the rectum, following the use of the apparatus according to the invention
Figure 4:
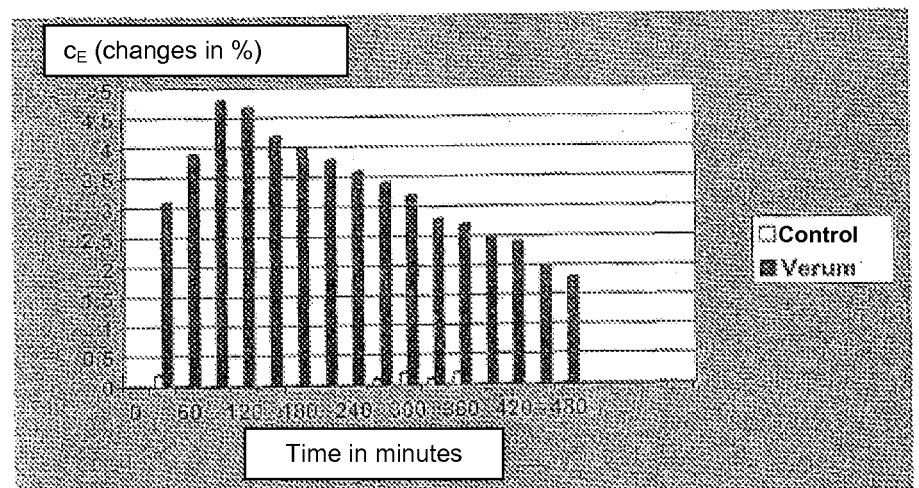
FIG. 4 shows a diagram relating to the feature change in endorphin concentration $c_E$ in the target tissue, i.e. subcutaneous tissue, following the use of the apparatus according to the invention

As can be seen in the illustration in FIG. 3 and FIG. 4, in the verum group, unlike in the control group, after an increase to a maximum at 90 minutes and a percent change of more than 6% and about 5%, respectively, the decay proceeds very slowly, and even after the examination period has ended, the level is still significantly higher than the initial value. Also here, the neurovegetative feature change lies in an unexpected increase and a very long duration of the effect. What is particularly impressive is that electromagnetic fields pulsed in this manner are not only effective in the microcirculation, but also here, e.g. in the neurovegetative system.

Figure 5:
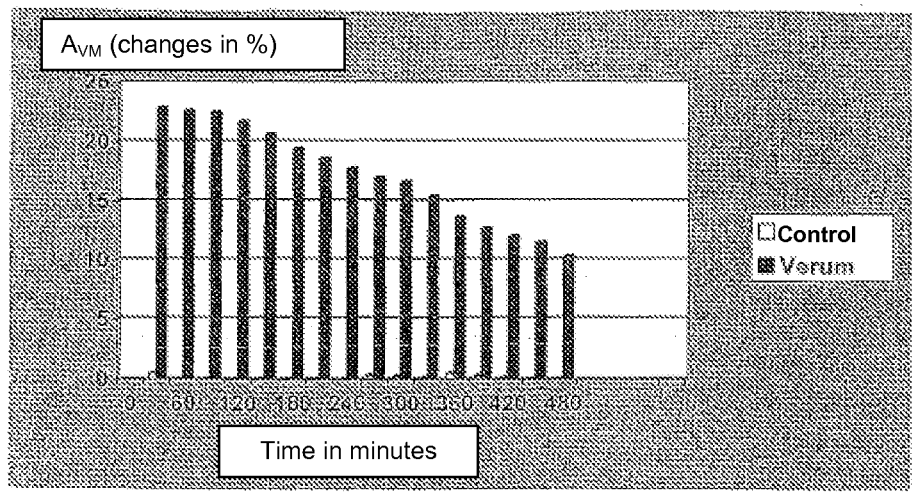
FIG. 5 shows a diagram relating to the $A_{VM}$ feature in the target tissue, i.e. muscle layer of the rectum, following the use of the apparatus according to the invention
Figure 6:
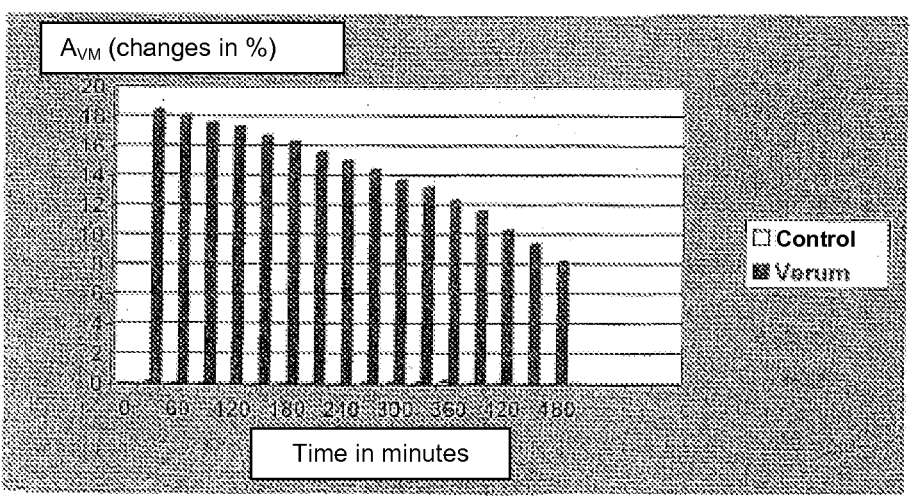
FIG. 6 shows a diagram relating to the $A_{VM}$ feature in the target tissue, i.e. subcutaneous tissue, following the use of the apparatus according to the invention.

3. Surface area below the envelope of the originary amplitude-frequency spectrum of the spontaneous arteriolar vasomotion, $A_{VM}$, in the microcirculation of a defined tissue volume unit (V=2000 µm³) in the target tissues, i.e. muscle layer of the rectum and subcutaneous tissue As can be seen in the illustration in FIG. 5 and FIG. 6, the verum group, unlike the control group, showed a significantly increased change of 23% and 18%, respectively, 30 minutes after treatment, and also the decay process was very slow and, at the end of the examination period, the value was still at 8-10%, such that the initial value was expected to be reached only several hours afterwards. Also here, in addition to the unexpectedly high level of the changes, which was 10-15% above the expected value, the decay time of the changes was again surprisingly long.

Overall, the apparatus according to the invention serves to achieve significant changes concerning features of the microcirculation of the blood as well as immunological, neurovegetative, neurological features and features of the central-nervous regulation of the circulatory system. The values are 10-15% higher than expected and, in particular, the effect achieved by the treatment lasts significantly longer.

Example 2

Comparative Example

The apparatus of the present invention is compared with the apparatus according to WO 2008/25731.

An apparatus and a coil mat as in Example 1 are used.

Test persons: male, aged 45-55 years, as part of a physical therapy and fitness scheme.

Verum group: 12 test persons, comparative group: 12 test persons, selected by means of a random generator.

Treatment interval: 30 days (treatments done blindfolded), measuring interval: also 30 days (equidistant and at the same time of day).

(a) Treatment of the verum group, lying down on the coil mat and with the pulse sequence (combined oscillations with an arcuate shape) in each case:

| Sequence 1: | 0 µT | 3 s | |
|---|---|---|---|
| Sequence 2: | 30 µT | 20 s | 33 Hz |
| Sequence 3: | 90 µT | 150 ms | 33 Hz |
| Sequence 4: | sequences 2 and 3 are repeated three times; | | 33 Hz |
| Sequence 5: | 0 µT | 3 s | |
| Sequence 6: | 25 µT | 18 s | 12 Hz |
| Sequence 7: | 70 µT | 120 ms | 12 Hz |
| Sequence 8: | 25 µT | 20 s | 12 Hz |
| Sequence 9: | 70 µT | 120 ms | 12 Hz |
| Sequence 10: | 0 µT | 2 s | | repetition of the pulse sequence for a total of 15 minutes of treatment 2-hour break another repetition of the pulse sequences as above for 15 minutes.

Measurements are taken on days 0, 5, 10, 15, 20, 25 and 30.

(b) Treatment of the comparative group, lying down on the coil mat and with the pulse sequence according to WO 2008/025731 (combined oscillations with an arcuate shape) in each case:

Base pulse: 60 µT, pulse width: 30 ms

Additional pulse: 180 µT, pulse width: 150 ms

Frequency of the additional pulse: 3 per minute

Overall frequency: 30 Hz

Duration of treatment: 2×25 minutes with a 2 h break in between

Frequency and continuation of treatment: daily for 30 days

Measurements on days 0, 5, 10, 15, 20, 25, 30

(c) Evaluation methods

Vital microscopic examination unit with computer-based image processing (KONTRON system), vital microscopic reflection spectrometry (SPEX system), combined Laser Doppler microflow measurement and white-light spectroscopy (LEA system).

(d) Features used for evaluation spontaneous arteriolar vasomotion, AVM (surface area below the envelope of the originary amplitude-frequency spectrum of the small-calibre arteriolar vasomotion), number of nodal points that are currently perfused with blood cells in the defined capillary network, nNP, venular oxygen utilization, $\Delta pO_2$, flow rate in the initial lymph vessels, QL.

Target tissue: intestine (muscle layer of the rectum).

Biometry:

WILCOXON rank sum test ($\alpha=5\%$)

TABLE 1

Spontaneous arteriolar vasomotion, AVM

| | Change in % by days | | | | | |
|---|---|---|---|---|---|---|
| | 0 | 5 | 10 | 15 | 20 | 25 | 30 |
| Comparative example 2(a) INVENTION | — | 14.8 | 20.9 | 24.6 | 25.1 | 25.4 | 25.8 |
| Comparative example 2(b) WO2008/025731 | — | 6.2 | 14.6 | 15.2 | 15.5 | 15.6 | 15.6 |

TABLE 2

Number of nodal points perfused with blood cells, nNP

| | Change in % by days | | | | | |
|---|---|---|---|---|---|---|
| | 0 | 5 | 10 | 15 | 20 | 25 | 30 |
| Comparative example 2(a) INVENTION | — | 9.8 | 15.5 | 21.0 | 25.7 | 26.8 | 27.2 |
| Comparative example 2(b) WO2008/025731 | — | 4.9 | 9.6 | 13.9 | 15.2 | 15.6 | 15.7 |

TABLE 3

Venular oxygen utilization, $\Delta pO_2$

| | Change in % by days | | | | | |
|---|---|---|---|---|---|---|
| | 0 | 5 | 10 | 15 | 20 | 25 | 30 |
| Comparative example 2(a) INVENTION | — | 9.4 | 15.1 | 20.9 | 25.6 | 27.7 | 29.2 |
| Comparative example 2(b) WO2008/025731 | — | 5.0 | 8.8 | 14.4 | 15.8 | 18.1 | 18.3 |

TABLE 4

Flow rate in the initial lymph vessels, QL.

| | Change in % by days | | | | | |
|---|---|---|---|---|---|---|
| | 0 | 5 | 10 | 15 | 20 | 25 | 30 |
| Comparative example 2(a) INVENTION | — | 18.1 | 23.0 | 29.3 | 32.1 | 36.3 | 38.6 |
| Comparative example 2(b) WO2008/025731 | — | 4.5 | 7.9 | 9.9 | 11.6 | 14.8 | 15.2 |

The comparison shows significant differences between the state-of-the-art apparatus according to WO 2008/025731 and the invention for all four measured features of the microcirculation of the blood. The QL feature is partly 2 to 3 times higher, other features 1.5 to 2 times.

The invention claimed is:

1. An apparatus for stimulating homeostatic autoregulatory mechanisms in the organism, comprising a pulse generator, a control device and a field generation device, characterized in that the pulse generator is designed to interact with the control device and the field generation device so as to generate a pulsed electromagnetic field by emitting pulse sequences, wherein the pulse sequences on a time axis starting with zero are as follows:

Sequence 1: 0 µT for 2-5 seconds,
Sequence 2: 3-35 µT base signal for 18-22 seconds,
Sequence 3: 30-120 µT additional signal for 100-200 milliseconds,
Sequence 4: sequences 2 and 3 are repeated two to three times,
Sequence 5: 0 µT for 2-5 seconds after 60-75 seconds on the time axis,
Sequence 6: 3-35 µT base signal for 18-22 seconds,
Sequence 7: 30-120 µT additional signal for 100-200 milliseconds,
Sequence 8: 3-35 µT base signal for 18-22 seconds,
Sequence 9: 30-120 µT additional signal for 100-200 milliseconds,
Sequence 10: 0 µT for 2-5 seconds, repeating all sequences multiple times in the specified order after 100 to 130 seconds on the time axis, wherein the frequency in sequences 2 and 3 ranges from 30-35 Hz and the frequency in sequences 6 to 9 ranges from 8-15 Hz, the additional signal in all frequencies is at least 20 µT above the base signal and the amplitudes of the individual pulses follow an exponential function or arcuate, rising and falling envelope curses with a harmonic or anharmonic pattern.

2. An apparatus according to claim 1, wherein the field generation device is a coil mat.

3. An apparatus according to claim 2, wherein in said coil mat, multiple individual electromagnetic coils are distributed evenly throughout the entire surface area of the mat in order to produce a flat magnetic field.

4. An apparatus according to claim 3, wherein the individual coils are designed as conductor loops with an identical surface area and/or different surface areas.

5. An apparatus according to claim 1, wherein in said pulse sequences the additional signal is at least 35 µT above the base signal, in particular at least 45 µT above the base signal, in all sequences.

6. An apparatus according to claim 1, wherein the region on the time axis for the repetition of all sequences is 115 to 125 seconds.

7. An apparatus according to claim 1, wherein in the pulsed electromagnetic field generated, the level of the base signal, the level of the additional signal and the frequency with which the pulse sequences are repeated are controlled as a function of values present, selected from microcirculatory functional features, neurovegetative features, immunological features, features of the humoral and central-nervous regulation of the circulatory system as well as neurological features.

8. A prophylactic or therapeutic method for stimulating local and higher homeostatic autoregulatory mechanisms in the organism, characterized in that the body or a part of the body of a patient is exposed to a pulsed electromagnetic field, wherein the pulse sequences on a time axis starting with zero are as follows:

Sequence 1: 0 µT for 2-5 seconds,
Sequence 2: 3-35 µT base signal for 18-22 seconds,
Sequence 3: 30-120 µT additional signal for 100-200 milliseconds,
Sequence 4: sequences 2 and 3 are repeated two to three times,
Sequence 5: 0 µT for 2-5 seconds after 60-75 seconds on the time axis,
Sequence 6: 3-35 µT base signal for 18-22 seconds,
Sequence 7: 30-120 µT additional signal for 100-200 milliseconds,
Sequence 8: 3-35 µT base signal for 18-22 seconds,
Sequence 9: 30-120 µT additional signal for 100-200 milliseconds,
Sequence 10: 0 µT for 2-5 seconds, repeating all sequences multiple times in the specified order after 100 to 130 seconds on the time axis over a period of 5-20 minutes, wherein the frequency in sequences 2 and 3 ranges from 30-35 Hz and the frequency in sequences 6 to 9 ranges from 8-15 Hz, the additional signal in all frequencies is at least 20 µT above the base signal and the amplitudes of the individual pulses follow an exponential function or arcuate, rising and falling envelope curves with a harmonic or anharmonic pattern.

9. A method according to claim 8, wherein the duration of treatment ranges from a one-off treatment to a twice-daily treatment for 5-15 minutes and 1 to 90 days, wherein interruptions of 2-5 days can be planned.

10. The method according to claim 8, wherein microcirculatory functional features, neurovegetative features, immunological features, features of the humoral and central-nervous regulation of the circulatory system as well as neurological features are stimulated.

\* \* \* \* \*